United States Patent [19]

Staudinger

[11] Patent Number: 5,792,091
[45] Date of Patent: Aug. 11, 1998

[54] SELF-ADHESIVE READY-TO-USE BANDAGE FOR ELBOWS

[75] Inventor: Peter Staudinger, Tornesch, Germany

[73] Assignee: Beiersdorf AG, Hamburg, Germany

[21] Appl. No.: 676,026

[22] Filed: Jul. 5, 1996

[51] Int. Cl.⁶ .................................................. A61F 5/00
[52] U.S. Cl. ........................... 602/57; 602/20; 602/62
[58] Field of Search ........................... 602/41–45, 52, 602/53, 54–56, 57, 79, 20, 26, 60, 61, 62; 128/887–889

[56] References Cited

U.S. PATENT DOCUMENTS

| | | |
|---|---|---|
| 2,983,272 | 5/1961 | Hunstiger . |
| 3,245,406 | 4/1966 | Chardack ................................. 602/79 |
| 4,748,975 | 6/1988 | Yashima . |
| 5,139,476 | 8/1992 | Peters . |
| 5,170,781 | 12/1992 | Loomis ................................. 602/42 X |

FOREIGN PATENT DOCUMENTS

| | | |
|---|---|---|
| 0 519 135 A | 12/1992 | European Pat. Off. . |
| 0 739 617 A2 | 10/1996 | European Pat. Off. . |
| 2 307 518 | 11/1976 | France . |
| 2 242 818 | 2/1991 | United Kingdom . |
| WO 93/00788 | 1/1993 | WIPO . |

Primary Examiner—Richard J. Apley
Assistant Examiner—Kim M. Lee
Attorney, Agent, or Firm—Sprung Kramer Schaefer & Briscoe

[57] ABSTRACT

A ready-to-use bandage for supporting and partially fixing an elbow. The self-adhesive bandages comprise an elongated strip having two narrow strips formed by a longitudinal incision and terminating in a recess in the form of a triangle having a vertex located at the terminal end of the incision and a base transverse to the longitudinal direction of the bandage.

7 Claims, 2 Drawing Sheets

SELF-ADHESIVE READY-TO-USE BANDAGE FOR ELBOWS

The invention relates to a ready-to-use bandage which has a self-adhesive coating on one side and which is used for supporting, fixing, stabilizing and relieving the strain on the elbow joint.

BACKGROUND OF THE INVENTION

The functional bandaging technique, so-called taping, is a common treatment method for the prevention and therapy of injuries, disorders and changes of the locomotor system. The aim of taping is to specifically simulate the individual soft parts and capsular ligament structures and to selectively support their functions.

The actual tape bandage is applied in the form of several bands, so-called bridles, in strip formation, using preferably nonelastic material, sometimes combined with elastic material, and then satisfies the functions of support and relief.

However, bandages of this type require specialist ability and a great deal of experience and therefore cannot generally be applied by someone inexperienced in taping.

SUMMARY OF THE INVENTION

The object of the invention was therefore to make available a ready-to-use bandage which, by virtue of its design, its material and the self-adhesive properties, substantially satisfies the requirements of a full tape bandage and which in addition can be applied easily and quickly by the user.

DESCRIPTION OF PREFERRED EMBODIMENTS

The elongate strip is approximately 1 m long in all, preferably approximately 90 cm, and is approximately 8 cm wide, with the undivided section being approximately 50 cm long and the divided section approximately 40 cm long. The dividing cut is generally made in the centre of the strip so that the two resulting narrow strips are approximately 4 cm wide.

The bandage preferably consists of a longitudinally elastic woven or knitted fabric which can also have, if appropriate, a slight transverse elasticity, in particular on a cotton base. The longitudinal elasticity preferably corresponds to that of so-called short extension bandages, i.e. bandages with an extensibility of about 60%–90%.

It has proven very favourable if a recess in the form of a triangle is located at the inner end of the incision. In this way, the fit of the bandage is improved and the application made easier. The triangle is arranged in such a way that its vertex represents the end of the incision and its base extends transverse to the longitudinal direction of the bandage. The triangle is preferably isosceles and also approximately equilateral. Its base amounts to approximately one third of the width of the bandage.

It is likewise advantageous if the ends of the bandage are rounded. This makes it easier to remove the bandage after use. If appropriate, it is also possible for just one end to be rounded, and namely in particular the end of the undivided wide section.

On its side facing the skin, the bandage is coated with one of the known readily adhering self-adhesive compositions based on rubber or synthetic polymers. These should-preferably be air-permeable and water-vapour-permeable and should have good skin compatibility.

Until the bandage is used, this adhesive layer is covered with a sheet, material treated so as to be adhesive-repellent, for example siliconized paper or plastic film.

It has proven favourable in this case to design this cover in several parts, preferably in three parts. In this case, one part, which is also strip-shaped, covers the undivided section of the strip of the bandage, and two further strip-shaped parts cover the narrower strips of the divided side. As an aid to application, the cover parts can be colour-marked or numbered.

Figure 2:
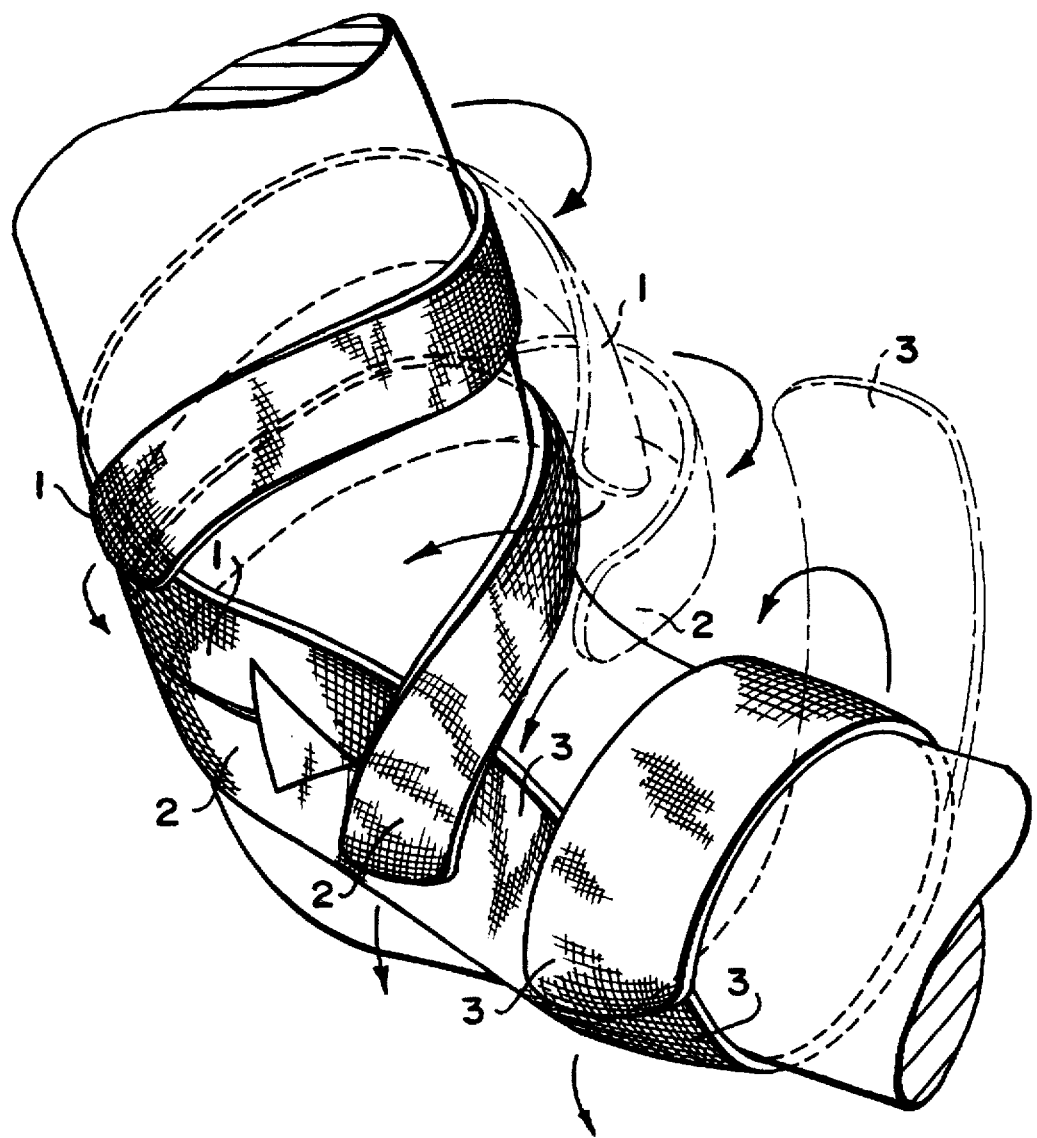
FIG. 2 is a view showing the bandage in place on an elbow.

When applying the bandage, the latter is placed, as shown in FIG. 2, in such a way that the triangular recess lies lateral of the bend of the elbow, with the vertex of the triangle pointing upward. First, the cover paper is removed from the undivided section (3) of the strip, and the latter is guided, from proximal to distal, over the epicondyle to the volar forearm and adhesively secured. The rest of this bridle is then passed in an elliptical configuration around the forearm, and the bridle ends up lying upon itself on the outer side of the elbow and thus secures itself. The elliptical turn is applied without any pulling in order to avoid constriction or obstruction.

After the cover paper has been removed, the narrow bridles of the slotted part of the bandage are first applied around the upper arm without pulling, beginning with the proximal bridle (1), and in the most expedient case the bridle (1) fixes itself on the upper arm.

The outer bridle (2) is finally placed below the bridle (1) around the distal upper arm and ends on the outer side of the elbow, most expediently on the epicondyle.

The functions of the individual bridles, if they are applied as illustrated, can be described as follows:

The narrow bridle (1) acts as a fixation bridle and extension-limiting reinforcement. The narrow bridle (2) serves as a relief bridle for the epicondyle, and the wide bridle (3) serves as an extension-limiting bridle on the forearm.

Considered as a whole, the applied bandage protects, fixes, stabilizes and also relieves the strain on the elbow joint in a manner adapted to the anatomical functioning.

Figure 1:
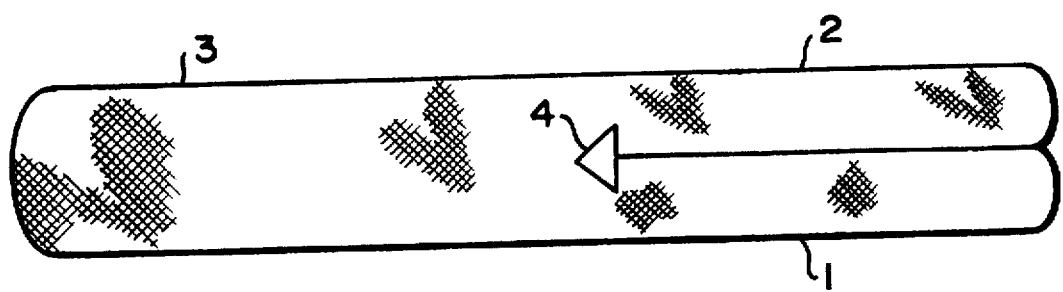
FIG. 1 is a top view of the bandage of the invention.

The bandage according to the invention is illustrated by way of example in FIG. 1. Here, (1) and (2) denote the two narrow bridles of the divided section, and (3) denotes the wide bridle of the undivided section. The triangular recess is designated by (4).

FIG. 2 shows the bandage in the applied state, with the arrows indicating the dressing direction.

I claim:

1. A self-adhesive ready-to-use bandage for supporting and partially fixing an elbow joint, comprising an elongated strip of longitudinally elastic fabric having a continuous layer of self-adhesive coated on one side, said strip having a center, and which elongated strip on one end having an incision running in the longitudinal direction as far as approximately the center of the elongated strip forming two narrow strips and an opposite end of the elongated strip defining a portion not having an incision, the incision terminating in a recess in the form of a triangle having vertex located at the terminal end of and in line with the incision and a base extending transverse to the longitudinal direction of the bandage beyond the incision and the incision and internal of the outer edges of the bandage, said triangle being positioned such that during use, a portion of the epicondylis humerus radialis in uncovered and available for treatment.

2. As self-adhesive bandage according to claim 1, wherein the portion of the elongated strip not having an incision (3) is approximately 50 cm long and 8 cm wide, and the two narrow strips (1) and (2) formed by the incision are approximately 40 cm long and in each case 4 cm wide.

3. A self-adhesive bandage according to claim 1, wherein the base of the triangle (4) is approximately ⅕ of the width of the bandage.

4. A self-adhesive bandage according to claim 1, wherein the ends of the strips (1), (2) and (3) are rounded.

5. A self-adhesive bandage according to claim 1, characterized in that it is covered on its self-adhesive side with an adhesive-repellent material.

6. A self-adhesive bandage according to claim 5, wherein the adhesive-repellent material is designed in three parts, with one part covering the undivided section (3) and each of two further parts covering the narrow strips (1) and (2).

7. Self-adhesive bandage according to claim 1, wherein the longitudinal elasticity has an extensibility of about 60–90%.

* * * * *

UNITED STATES PATENT AND TRADEMARK OFFICE
CERTIFICATE OF CORRECTION

PATENT NO. : 5,792,091
DATED : August 11, 1998
INVENTOR(S) : Peter Staudinger

It is certified that error appears in the above-identified patent and that said Letters Patent are hereby corrected as shown below:

| | |
|---|---|
| Title Page [56] Foreign Patent Documents | After "0 519 135 A" and before "12/1992" insert -- 1 -- |
| Title Page [56], Foreign Patent Documents | After "2 242 818" and before "2/1991" insert -- A -- |
| Col. 3, Line 1 | Delete "and the incision" |
| Col. 3, Line 4 | Delete "in" and substitute -- is -- |
| Col. 3, Line 5 | Delete "As" and substitute -- A -- |
| Col. 4, Line 1-2 | Delete "characterized in that" and substitute -- wherein -- |

Signed and Sealed this

Eleventh Day of January, 2000

Attest:

Q. TODD DICKINSON

Attesting Officer

Acting Commissioner of Patents and Trademarks